United States Patent [19]

Cheminal et al.

[11] Patent Number: 4,658,070
[45] Date of Patent: Apr. 14, 1987

[54] PROCESS FOR THE SYNTHESIS OF 2,2,2-TRIFLUOROETHANOL

[75] Inventors: Bernard Cheminal, Lyons; Henri Mathais, Saint Didier au Mont D'Or, both of France

[73] Assignee: Atochem, France

[21] Appl. No.: 854,103

[22] Filed: Apr. 21, 1986

[30] Foreign Application Priority Data

Apr. 23, 1985 [FR] France .................. 85 06121

[51] Int. Cl.$^4$ ............................................. C07C 31/38
[52] U.S. Cl. ................................. 568/842; 402/150
[58] Field of Search .......................................... 518/842

[56] References Cited
FOREIGN PATENT DOCUMENTS 997810 7/1965 United Kingdom ................ 568/842

Primary Examiner—Howard T. Mars
Attorney, Agent, or Firm—Sigalos & Levine

[57] ABSTRACT

The process for synthesizing 2,2,2-trifluoroethanol by liquid phase catalytic hydrogenation of a compound of formula:

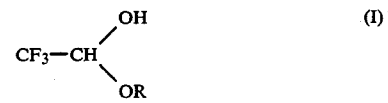

(I)

in which R is a hydrogen atom or a linear or branched alkyl radical containing from 1 to 8 carbon atoms and optionally partially fluorinated, comprising carrying out the hydrogenation in the presence of a nickel catalyst and in the presence of an aliphatic tertiary amine as a cocatalyst.

14 Claims, No Drawings

PROCESS FOR THE SYNTHESIS OF 2,2,2-TRIFLUOROETHANOL

BACKGROUND OF THE INVENTION

The present invention relates to the manufacture of 2,2,2-trifluoroethanol by hydrogenolysis of 2,2,2-trifluoroacetaldehyde (fluoral) hydrates or hemiacetals.

An important industrial source of fluorinated primary alcohols such as 2,2,2-trifluoroethanol, which has uses in a wide variety of applications such as energy recovery (absorption heat pumps), pharmaceutical products (anaesthetics) and solvents, is based on the reduction of the corresponding acid (in this case trifluoroacetic acid) or of a derivative (ester, acid chloride, anhydride, amide) with hydrogen in the presence of a catalyst which is chosen in most cases from the precious metal group (rhodium, ruthenium, platinum, palladium). Among the chief techniques employed, there may be mentioned the hydrogenation of trifluoroacetic anhydride (U.S. Pat. No. 4,255,594), the hydrogenation of trifluoroacetic acid (Patents: U.S. Pat. No. 4,273,947, FR 2,544,712, and FR 2,545,481), the hydrogenation of esters of trifluoroacetic acid (Patent EP 36,939), the hydrogenation of trifluoroacetamide [M. Gilman, J.A.C.S., 70, 1281-2 (1948)], and the hydrogenolysis of trifluoroacetyl chloride (U.S. Pat. No. 3,970,710). Apart from the disadvantage of poor catalyst behavior with time, these processes have the economic disadvantage of relying on an oxidation of the starting materials (chlorinated in most cases), to provide access to the acid or to one of its derivatives, followed by a reduction of this acid to alcohol; this additional stage represents a very serious burden on the profitability of these processes.

Another group of processes consists in hydrogenating fluoral or one of its derivatives. The yield produced by liquid phase hydrogenation (80° C. at 95 bar) of fluoral hydrate over a nickel catalyst (Patent FR 1,399,290) is indifferent; the catalyst life is not mentioned and the reaction requires a large quantity of catalyst (16% by weight of pure nickel, based on the fluoral) under very severe operating conditions. Mention can also be made of U.S. Pat. No. 2,982,789, which describes the gas phase hydrogenation of fluoral hydrochloride: CF$_3$CH(Cl)OH originating from a first stage of a hydrogenolysis (Rosenmund reaction) of trifluoroacetyl chloride over a palladium catalyst. The fluoral hydrogenation catalyst, which consists of copper chromite deposited onto calcium fluoride, and whose behavior with time is not mentioned, operates at about 250° C. and enables the fluoral intermediate to be converted only incompletely (approximately 60-65%); in addition, recycling the unconverted fluoral hydrochloride is a highly hazardous operation because of its thermal instability, the decomposition:

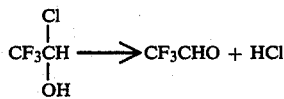

being promoted at 30° C. and above by a temperature rise or a pressure reduction. Lastly, there may be mentioned the gas phase hydrogenation of fluoral (U.S. Pat. No. 3,468,964) in the presence of a palladium catalyst deposited onto alumina at a low temperature (peak temperature: 140° C.); the relatively poor yield of trifluoroethanol (86%) and the need to regenerate the catalyst very frequently at 200° C. in pure oxygen as well as the extreme difficulty of conveying fluoral in a pure state (polymerization) make the process unattractive.

SUMMARY OF THE INVENTION

The present invention makes it possible to overcome all of these disadvantages by offering a simple, flexible and particularly economical technique for producing 2,2,2-trifluoroethanol, and this even from a crude starting material which is easy to prepare and to transport, without damage to catalyst life, or to the yield, or to the productiveness.

The process according to the invention comprises subjecting a compound of general formula:

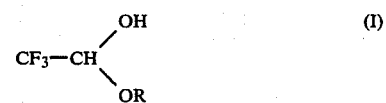

in which R is a hydrogen atom or a linear or branched alkyl radical containing from 1 to 8 carbon atoms and optionally partially fluorinated, to a liquid phase hydrogenolysis in the presence of a nickel catalyst and an aliphatic tertiary amine as a cocatalyst.

DETAILED DESCRIPTION

The compounds of formula (I) which are used as starting materials in the process according to the invention, may be obtained, in a crude state, in a known manner by the action of water (R=H) or of an alcohol (R=optionally substituted alkyl) with fluoral, according to the following reaction scheme:

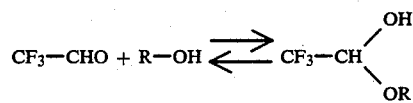

As examples of alkyl radicals R, there may be mentioned, more especially, methyl, ethyl, n-propyl, isopropyl, n-butyl, sec-butyl, n-hexyl, 2-ethylhexyl, 2,2,2-trifluoroethyl, and 1,1,1,3,3,3-hexafluoro-2-propyl radicals.

The thermal stability of the compounds obtained depends substantially on the temperature, the pressure, and their chemical nature. In general, the hydrates (R=H) are stable but difficult to purify by distillation. The hemiacetals (R=alkyl) are proportionately more stable the lower the number of carbon atoms in R; their purification occasionally demands a distillation under a slightly reduced pressure (200 torr) and with a short residence time (falling film evaporation). For example, the crude hemiacetal CF$_3$—CH(OH)—OCH$_3$ is stable and may be distilled (boiling point: 96° C./760 torr) at atmospheric pressure without decomposition, and consequently isolated from the (denser) chlorinated compounds and from hydrochloric acid. A product assaying at ≧99.9% is then obtained when an excessively long residence time (approximately several minutes) in the boiler of the distillation apparatus is avoided. On the other hand, the hemiacetal CF$_3$—CH(OH)—OCH$_2$CF$_3$, which is highly unstable, cannot be purified by distillation. Nevertheless, in accordance with the present invention, it can be used as such in the crude state, that is to say, in the form of a mixture comprising from 1 to 10 moles percent of a chlorinated hemiacetal $CF_2Cl-CH(OH)-OCH_2CF_3$, from 0.1 to 10 moles percent of a dichlorinated hemiacetal $CFCl_2-CH(OH)-OCH_2CF_3$ and from 1 to 10 moles percent of hydrochloric acid.

The nickel content of the catalyst used in the process according to the invention may vary between 30% and 90% by weight, but a catalyst containing approximately 60% of nickel is preferably used. Obviously, the quantity of catalyst to be used depends on its nickel content. In the case of a commercial catalyst containing 64% of nickel, this quantity may vary between 0.2% and 7.5% and, preferably, between 0.5% and 2% relative to the weight of the crude substrate (hydrate or hemiacetal) which is employed.

The nickel catalyst used may be, for example, Raney nickel obtained by an alkali metal (especially sodium) attack on a 50/50 nickel/aluminium alloy, followed by washing with water, and, if appropriate, with a dilute aqueous solution of acetic acid. Preferably, a commercial nickel catalyst deposited on a conventional support such as silica or, preferably, kieselguhr, is employed. This type of catalyst is generally supplied in a stabilized form (prereduced with a slight surface oxidation) so as to make its transport and its handling easier and also to make it nonpyrophoric.

The catalyst may be used as such, with or without a preliminary activation in the reactor, before the hydrogenolysis operation. This optional activation may be carried out, for example, at a temperature of between 140° and 200° C., preferably between 170° and 180° C., under a hydrogen pressure of 30 to 45 bar. Such an activation is, however, needed when a stabilized commercial catalyst is used.

After each hydrogenolysis operation, the catalyst may be usefully separated from the reaction mixture by settling, and then filtration, followed by one or more washings with water or with the pure alcohol which is synthesized in the process. It may also be left to remain in contact with the reaction mixture (preferably for less than 48 hours), allowed to settle, and the reaction mixture then being separated off by draining under a hydrogen atmosphere and a following operation being restarted with the same catalyst charge. The magnetic nature of the catalyst can also be used to advantage to separate it from the reaction mixture.

The reactants (substrate+cocatalyst) may be introduced with the catalyst at the beginning of the reaction. However, to avoid an excessively fast deactivation of the catalyst with time, it is preferable to introduce the mixture of the reactants gradually into a mixture consisting of water or, alternatively, the crude alcohol originating from the preceding synthesis (or purified alcohol) and catalyst.

The hydrogenolysis may be carried out at a temperature of between about 150° and 200° C.; preferably between 170° and 180° C., and at a pressure of between approximately 20 and 50 bars, preferably between 30 and 45 bars.

In the case where, in accordance with a preferred form of the process according to the invention, the reactants (substrate+cocatalyst) are added to the hydrogenolysis reactor gradually, the addition period may vary between about 0.2 and 5 hours, preferably between 0.75 and 1.25 hours. To avoid an excessively fast deactivation of the catalyst, it is especially advantageous for the rate of addition of the reactants to correspond as precisely as possible to the rate of hydrogenolysis. The most suitable control system for arriving at this result consists in using the hydrogen consumption (itself related to the hydrogen flow rate or pressure) to control the output of the injection pump; as the catalyst undergoes a slow deactivation with time, its slight loss in activity can thus be compensated by a corresponding increase in the addition time of the reactants; this considerably increases the flexibility of the process, improving its economy at the same time.

The cocatalyst used is a aliphatic tertiary amine of formula:

in which the symbols $R_1$, $R_2$, and $R_3$ can be identical or different and each denotes an alkyl radical; preferably a $C_1$ to $C_4$ alkyl radical, optionally substituted by a hyroxyl group. Although it is preferable to use dimethylethylamine or tributylamine, there may also be mentioned, by way of nonlimiting examples: trimethylamine, triethylamine, tri-n-propylamine, dimethylethanolamine, and triethanolamine.

The quantity of cocatalyst may vary within very wide limits depending on the purity of the substrate (hydrate or hemiacetal) subjected to the hydrogenolysis. Naturally, it is desirable to start with a substrate which is as pure as possible, but this is not always practicable; a less efficient fluorination catalyst leading to a higher content of chlorinated products, a secondary reaction of the alcohol making it necessary to absorb the carbonyl derivative at a low temperature, thus increasing the solubility of hydrochloric acid, chlorinated and fluorinated hydrates incapable of being separated by distillation, and the like. The quantity of cocatalyst to be used is generally between approximately 1.05 and 6 moles, preferably between 1.05 and 4 moles, per gram-atom of chlorine in the chlorinated by-products present in the crude starting material.

The solvent used may be water or any usual organic solvent (aliphatic ketones, ethers, glycols, chlorinated solvents), but the 2,2,2-trifluoroethanol provided by the process according to the invention is preferably used. It is also possible to use an aliphatic alcohol R-OH (R having the same meaning as above). The quantity of solvent to be used may vary from 0 to 100% relative to the weight of the substrate used and depends only on the geometry of the hydrogenolysis reactor (in particular to ensure excellent stirring) and on the intended productiveness.

The process according to the invention may be carried out in an apparatus of a conventional type; that is to say, an autoclave stirred by appropriate mechanical means, capable of operating under a pressure of 50 bars and fitted with a device for draining the catalyst suspension and the essential adjuncts (filter, pumps, hydrogen pressure control, and the like). Since the basic medium guarantees the absence of corrosion, the reactor may be constructed merely in stainless steel (NS 22 S).

The hydrogenolysis according to the invention can also be carried out in a continuous liquid phase over a fixed catalyst bed.

The 2,2,2-trifluoroethanol produced may be isolated and purified by conventional methods such as distillation and drying over a molecular sieve. Its purity may be determined by gas phase chromatography.

The invention will be further described in connection with the following examples which are set forth for purposes of illustration only. In these examples the catalyst used is a standard catalyst supplied by the Harshaw Company under the reference Ni 5132 P and it contains 64% of nickel deposited on kieselguhr and is in the form of a fine powder; all the particles of which have a diameter greater than 0.5 μm. Since this catalyst has been made nonpyrophoric by a slight surface oxidation to facilitate its handling and its transportation, an "in situ" activation with hydrogen is necessary before any test is started.

EXAMPLE 1

1.82 g of catalyst NI 5132 P, followed by 21 g of 2,2,2-trifluoroethanol are charged in succession into a 0.1-liter autoclave fitted with a magnetic bar stirring system. The reactor is closed, the enclosed air is purged with nitrogen, a slight pressure of hydrogen is introduced, and then the mixture is heated to approximately 175° C. with stirring and the hydrogen pressure is adjusted to 38 bars. Catalyst activation takes 20 minutes under these conditions.

A mixture is then added gradually (approximately 57 minutes) into the reactor, consisting of 2.1 g of dimethylethylamine (0.0287 mole) and 31.3 g of crude hemiacetal containing (on a molar basis) 95.5% of $CF_3-CH(OH)-O-CH_2-CF_3$ and 4.5% of $CF_2Cl-CH(OH)-O-CH_2-CF_3$ which corresponds to 0.151 mole and 0.007 mole respectively, the dissolved hydrofluoric acid representing $3.33 \times 10^{-5}$ mole.

The pressure drop corresponding to the consumption of hydrogen is then compensated by successive additions of hydrogen at between 35 and 45 bars. Once hydrogen absorption has ceased (after 65 minutes), the reaction mixture is quickly cooled and then, after it has been degassed in a receptacle maintained at about $-196°$ C. with liquid nitrogen, the reactor is opened and the reaction product, mixed with the catalyst, is transferred to a receptacle in which the catalyst suspension is allowed to settle. After separation of the catalyst, a sample of the hydrogenolysis product is analyzed. The pH of an aqueous solution is noted and inorganic analysis is used to determine the chloride ($Cl^-$) and fluoride ($F^-$) ions formed during the reaction.

Table I below collates the results obtained in this example and in Examples 2 to 6 that follow.

EXAMPLE 2

The method used is as in Example 1, but the hemiacetal is replaced by 32.4 g of crude fluoral hydrate, which has the following composition:

| | |
|---|---|
| $CF_3-CH(OH)_2$ | 0.244 mole |
| $CF_2Cl - CH(OH)_2$ + dissolved HCl | 0.0066 mole |
| dissolved HF | $4.91 \times 10^{-5}$ mole |
| $H_2O$ | 0.189 mole |

After one hour at 175° C. at approximately 32 to 45 bars, the reaction is complete and the yield of 2,2,2-trifluoroethanol is quantitative.

EXAMPLE 3

Example 2 is repeated, but with the use of only 0.36 g of catalyst. After 110 minutes at 175° C. at 37 to 46 bars of hydrogen, the reaction is complete and the yield of 2,2,2-trifluoroethanol is quantitative.

EXAMPLE 4

The method used is as in Example 1 with 0.38 g of catalyst, 0.32 g of pure dimethylethylamine ($4.38 \times 10^{-3}$ mole) and 40.1 g of crude fluoral hydrate which has the following composition:

| | |
|---|---|
| $CF_3-CH(OH)_2$ | 0.247 mole |
| $CF_2Cl-CH(OH)_2$ | 0.003 mole |
| dissolved HCl | $1.7 \times 10^{-5}$ mole |
| dissolved HF | $1.21 \times 10^{-4}$ mole |
| $H_2O$ | 0.619 mole |

After 95 minutes at 175° C. at 27 to 46 bars of hydrogen, the reaction is complete and the yield of 2,2,2-trifluoroethanol is quantitative.

EXAMPLE 5

Example 4 is repeated, but with the use of only 0.26 g of dimethylethylamine ($3.56 \times 10^{-3}$ mole). After 100 minutes at 175° C. at 29 to 46 bars of hydrogen, the reaction is complete and the yield of 2,2,2-trifluoroethanol is quantitative.

EXAMPLE 6

(a) Example 4 is repeated, but with dimethylethylamine replaced by 1.39 g of tributylamine ($7.5 \times 10^{-3}$ mole). The reaction is finished after 80 minutes at 175° C. at 33 to 48 bars of hydrogen.

(b) The catalyst originating from run (a) is reused for a new run carried out under the same condition, using the same quantities of crude hydrate and tributylamine. The reaction takes 95 minutes.

TABLE I

| EXAMPLE | pH | $Cl^-$ formed (per 100 moles of $C_2$*) | $F^-$ formed |
|---|---|---|---|
| 1 | 10.05 | 1.54 | 0.27 |
| 2 | 8.65 | 5.44 | 0.30 |
| 3 | 8.80 | 5.73 | 0.59 |
| 4 | 7.20 | 0.83 | 0.22 |
| 5 | 6.80 | 0.65 | 0.16 |
| 6(a) | 8.90 | 0.91 | 0.57 |
| 6(b) | 7.50 | 0.91 | 0.57 |

*$C_2$ denotes the compounds $CF_xCl_{3-x}CHO$, x being equal to 1, 2, or 3.

EXAMPLE 7

Comparative Example

Example 4 is repeated, but without the addition of dimethylethylamine. After 7 hours at 175° C. at 33 to 46 bars of hydrogen, only 40% of the fluoral has been converted to trifluoroethanol. The following data are obtained:

| | |
|---|---|
| pH | 5.1 |
| $Cl^-$ formed (per 100 mol of $C_2$) | 0.6 |
| $F^-$ formed (per 100 mol of $C_2$) | 0 |

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. The process for synthesizing 2,2,2-trifluoroethanol by liquid phase catalytic hydrogenation of a compound of formula:

in which R is a hydrogen atom or a linear or branched alkyl radical containing from 1 to 8 carbon atoms and optionally partially fluorinated, comprising carrying out the hydrogenation in the presence of a nickel catalyst and in the presence of an aliphatic tertiary amine as a cocatalyst.

2. The process of claim 1, wherein a mixture of a compound of formula (I) and of a cocatalyst is introduced gradually into a suspension of the catalyst in a solvent.

3. The process of claim 2, wherein, after the reaction has ceased, the reaction mixture is quickly cooled, and the catalyst is separated and is reused in a subsequent operation.

4. The process of claim 3, wherein the catalyst is separated off by filtration, and is then washed with water before reuse.

5. The process of claim 3, wherein, after the reaction mixture has been cooled, the catalyst is allowed to settle, and then the reaction liquid is drained off and the catalyst retained in the reactor is reused as such.

6. The process of claims 3 in which a compound of formula (I) is used in a crude state.

7. The process of claim 6 in which the operation is carried out at a temperature of from about 150° to 200° C.

8. The process of claim 7 in which the operation is carried out at a pressure of from about 20 to 50 bars.

9. The process of claim 8 in which the nickel content of the catalyst varies from about 30% to 90% by weight.

10. The process of claim 9 in which the catalyst is activated beforehand at a temperature of between about 140° and 200° C. at a hydrogen pressure of 30 to 45 bars.

11. The process of claim 10 in which the quantity of catalyst, expressed for a catalyst containing about 64% of nickel, is between about 0.2% and 7.5% relative to the weight of the hydrate or hemiacetal employed.

12. The process of claim 11 in which the quantity of cocatalyst is between about 1.05 and 6 moles per gram-atom of chlorine in the chlorinated by-products present in the crude compound of formula (I).

13. The process of claim 12, wherein the cocatalyst is an amine of formula $R_1-N(R_2)R_3$, in which each of $R_1$, $R_2$, and $R_3$ can be identical or different and each denotes an unsubstituted alkyl radical or an alkyl radical substituted by a hydroxyl group.

14. The process of claim 1, wherein a mixture of a crude compound of formula (I) and of a cocatalyst is introduced gradually into a suspension of a nickel catalyst in 2,2,2-trifluoroethanol and the hydrogenation is carried out at a temperature of from about 170° to 180° C. and a pressure of from about 30 to 45 bars; said catalyst containing about 64% of nickel and the amount used being from about 0.5% to 2% relative to the weight of said compound of formula (I); and said cocatalyst is an amine of the formula $R_1-N(R_2)R_3$, wherein each of $R_1$, $R_2$, and $R_3$ can be identical or different and each is an unsubstituted $C_1$ to $C_4$ alkyl radical or a $C_1$ to $C_4$ alkyl radical substituted by a hydroxyl group and the amount used being from about 1.05 and 4 moles per gram-atom of chlorine present in the chlorinated by-products present in the crude compound of formula (I).

* * * * *